United States Patent [19]

Seiler, Jr.

[11] 4,011,869
[45] Mar. 15, 1977

[54] TUBULAR CUTTING INSTRUMENT
[75] Inventor: William Seiler, Jr., Van Nuys, Calif.
[73] Assignee: David Kopf Instruments, Tujunga, Calif.
[22] Filed: Aug. 1, 1975
[21] Appl. No.: 600,897
[52] U.S. Cl. .............................. 128/276; 128/305; 83/582
[51] Int. Cl.² .................... A61M 1/00; A61F 9/00; A61B 17/32
[58] Field of Search ............. 83/582; 128/276, 305
[56] References Cited
UNITED STATES PATENTS

| 3,776,238 | 12/1973 | Peyman et al. ................. 128/305 |
| 3,882,872 | 5/1975 | Douvas et al. ................. 128/305 |
| 3,884,238 | 5/1975 | O'Malley et al. ................ 128/305 |

FOREIGN PATENTS OR APPLICATIONS 437,932  11/1926  Germany .......................... 128/305

*Primary Examiner*—Channing L. Pace

[57] ABSTRACT

A cutting instrument is provided, particularly applicable to vitreous surgery, having an elongated, tubular housing formed with a cutting orifice near its end. A resilient, inner tubular member is slidably mounted coaxially within the tubular housing. The tubular housing is bent in a manner to displace the cutting orifice in a direction toward the resilient, inner tubular member. As the end of the resilient, inner tubular member passes across the cutting orifice, it is resiliently urged into shearing contact with the cutting orifice.

7 Claims, 4 Drawing Figures

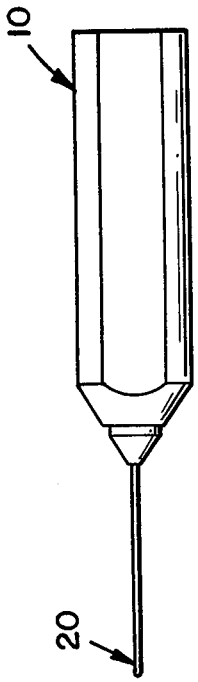
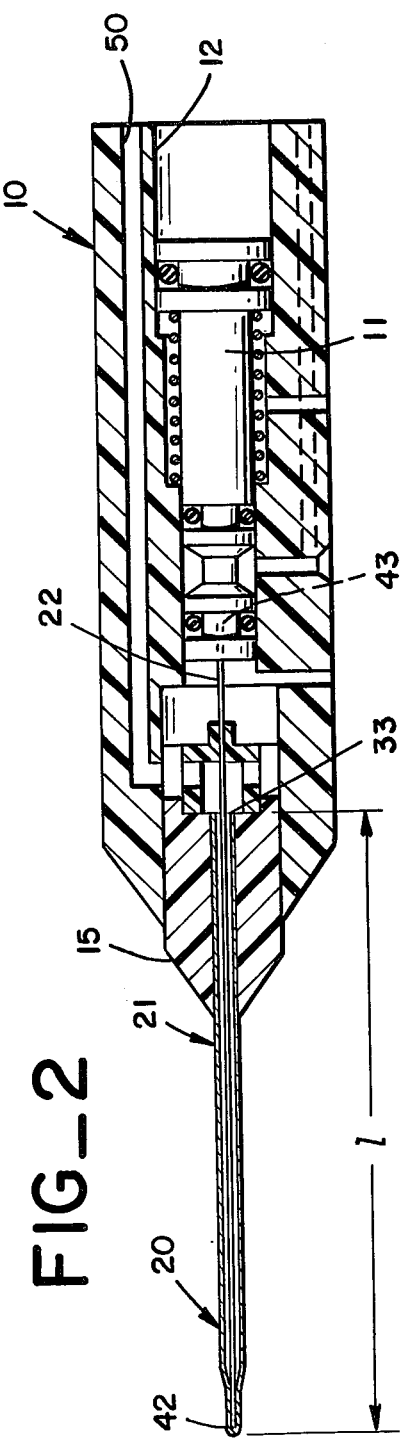
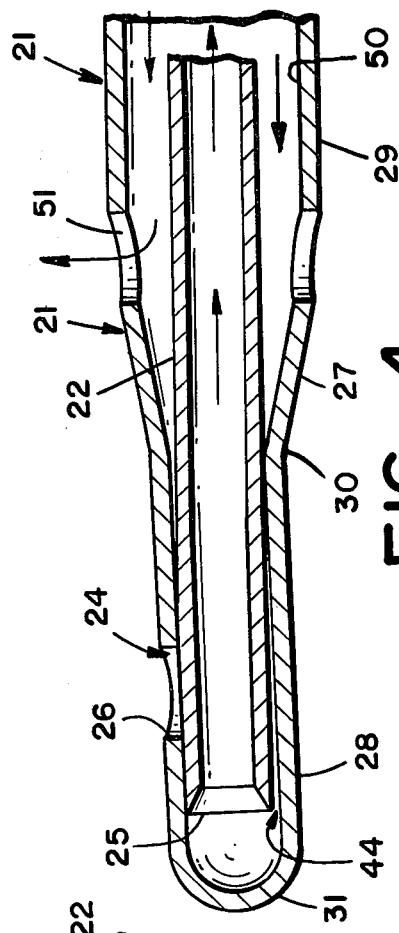
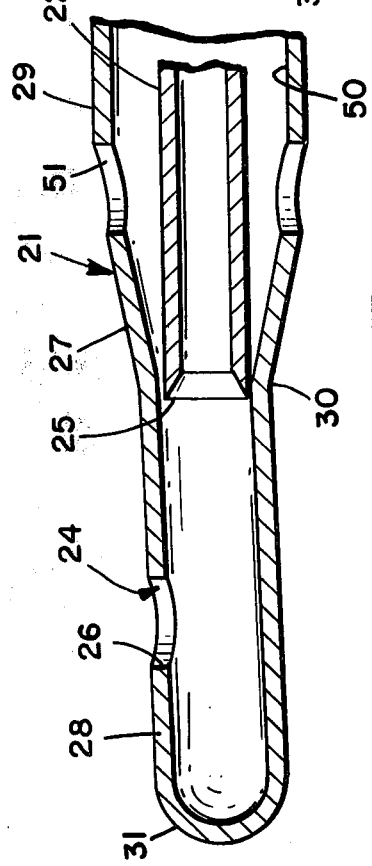

TUBULAR CUTTING INSTRUMENT

This invention relates generally to cutting instruments and more particularly to a cutting instrument useful in vitreous surgery.

The use of a pair of elongated tubes which reciprocate relative to each other to perform a cutting operation in vitreous surgery is known. O'Malley and Heintz U.S. Pat. No. 3,815,604, dated June 11, 1974, shows a cutting instrument for use in vitreous surgery in which the inner tube reciprocates in the direction of the longitudinal axis of the tubes. As the end of the inner tube reciprocates across a window in the elongated tube, the shearing action is performed. O'Malley et al teaches that the cutting action of the instrument is enhanced by the use of a flared inner member to maintain a snug fit between the two tubular members.

In practice, the O'Malley instrument has several deficiencies. It requires very close tolerances in machining. These close tolerances also tend to create excessive friction between the two tubular members in the operation of the device.

According to the present invention, a cutting instrument is provided which utilizes a pair of elongated tubes in which the outer tube has a cutting orifice. The cutting orifice in the outer tubular housing is displaced in a direction toward the resilient, inner tubular member such that as the end of the resilient, inner tubular member passes across said cutting orifice, it is resiliently urged into shearing contact with the cutting orifice.

A primary object of the invention is to provide a cutting instrument utilizing a pair of coaxial, elongated tubular members having improved cutting characteristics.

A further object of this invention is to provide a cutting instrument useful in vitreous surgery having improved cutting characteristics and which is relatively simple to manufacture.

A further object of the invention is to provide a cutting instrument useful in vitreous surgery in which a very efficient shearing action is provided with a minimum of friction between cutting surfaces.

Another object of the invention is to provide a cutting instrument useful in vitreous surgery in which the cutting surfaces are inherently selfsharpening.

Still another object of the invention is to provide a cutting instrument useful in vitreous surgery which is extremely reliable and simple to manufacture.

Other objects and advantages of the invention will become apparent from the following description of a preferred embodiment and the drawings wherein:

FIG. 1 is a side elevational view of a cutting instrument according to the present invention;

FIG. 2 is a side elevational view, in section, of the instrument shown in FIG. 1;

FIG. 3 is a schematic representation of the tubular members in one position according to the present invention and;

FIG. 4 is another schematic representation of the tubular members in a secondary position according to the present invention.

The embodiment of the invention shown in FIGS. 1–4 is particularly useful in vitreous surgery. The body 10 of the instrument is held in the surgeon's hand and the cutting tip 20 is inserted into the vitreous cavity for removing vitreous and the like from the eye. FIG. 2 generally shows the major components of the instrument. A piston 11 carries resilient, inner tubular member 22. Piston 11 slides in passageway 12 formed in body 10. Elongated tubular housing 21 is carried by a support member 15 which is rigidly mounted in the front section of body 10.

As shown in FIGS. 3 and 4, the instrument operates as follows. As resilient, inner tubular member 22 reciprocates with piston 11, the end 25 of member 22 passes across cutting orifice 24 formed in elongated tubular housing 21. When inner tubular member 22 is in the retracted position shown in FIG. 3, vitreous matter, lens material and the like which is to be severed, is drawn into the cutting orifice 24 by a vacuum applied through the inner diameter of member 22. This vitreous matter (including tough fibrous material approximately one micron thick) is severed by the end 25 of member 22 as it passes across the cutting orifice 24 to the advanced position shown in FIG. 4. Replacement saline solution is introduced through passageway 50 and orifice 51 to prevent collapse of the eyeball.

As shown best in FIGS. 3 and 4, the shearing action is improved by forming a bend in the elongated tubular housing 21 in such fashion to displace orifice 24 in a direction towards the inner tubular member 22. This displacement causes a bias effect on the resilient inner tubular member 22, which resiliently urges the end 25 of tubular member 22 into shearing contact with cutting orifice 24. The tough and extremely thin vitreous fibers are cut cleanly in this fashion, effectively minimizing the risk of tearing or pulling the vitreous fibers with the attendant risk of retinal detachment.

In order to assure that the end 25 of inner tubular member 22 is resiliently urged into shearing contact with cutting orifice 24, it is necessary to displace orifice 24 by an amount which exceeds the clearance between the inner tubular member 22 and tubular housing 21. As used herein, the term "clearance" refers to diametral clearance 44 between the outer diameter of tubular member 22 and the inner diameter of housing 21.

Housing 21 comprises a first cylindrical section 28 and second cylindrical section 29 joined by an intermediate, tapered section 27. The first section 28 has a smaller diameter than second section 29. In practice, it has been found that with the particular materials used, improved cutting action is achieved when cutting orifice 24 is displaced an amount which exceeds the clearance between members 21 and 22. Orifice 24 can be displaced in a direction toward member 22 as much as six times the clearance between members 21 and 22.

The material used for housing 21 is either 302 or 304 stainless steel, fully annealed, "condition A". The wall thickness is 0.005 inch. The inner diameter of section 21 is 0.038 inch. The outer diameter of section 29 is 0.070 – 0.073 inch. The tapered section is formed at an angle of 13° with the longitudinal axis of section 29. The cutting orifice 24 is 0.030 ± 0.002 inch diameter with sharp inside corners 26. Cutting orifice 24 is centered away from the intersection 30 of tapered section 27 and first section 28 a distance of 0.080 inch.

As shown in FIG. 3, a cap 31 is used to close off the end of housing 21. The length of housing 21, shown as "*l*" in FIG. 2, is 2.080 inches (exclusive of cap 31).

Orifice 24 is displaced by bending housing 21 about point 30. Point 30 is located at the intersection of tapered section 27 and first section 28 of housing 21 and is positioned 180° from the center of orifice 24. Housing 21, in the above embodiment, is bent to the extent to permanently displace end 33 (FIG. 2) 0.150 inch;

i.e., after the bending operation, if the first section 28 of housing 21 is placed with its longitudinal axis on a given straight line, the end 33 of section 29 would be displaced 0.150 inch from the given straight line.

The resilient, inner tubular member is made of 302 or 304 stainless steel, full hard, with 0.005 inch wall thickness and an outer diameter of 0.037 inch. Its length, from points 42 to 43 in FIG. 2, is 2.7 inch. End 25 of member 22 has a sharp corner formed by making a 60° cut relative to the longitudinal axis of member 22. The clearance between section 28 of housing 21 and member 22 ranges from 0.0007 – 0.0012 inch.

It is apparent that as end 25 of member 22 is resiliently urged against cutting orifice 24, member 22 will tend to flex as shown schematically in FIG. 4. By providing section 29 with a relatively large inner diameter, member 22 does not frictionally engage the inner diameter of section 29. The ends of member 22 in the position shown in FIG. 4 are secured at one end 42 by section 28 of housing 21 and on the other end 43 by piston 11.

The cutting surfaces (i.e., end 25 of member 22 and cutting orifice 24) are inherently self-sharpening due to the resilient urging of end 25 against orifice 24. The self-sharpening feature is enhanced by the use of hard stainless steel for inner member 22 and fully annealed stainless steel for housing 21. End 25 of member 22 tends to peel burrs and high spots off the corner 26 of orifice 24 when the instrument is first operated. The peeled-off material is sucked up through the interior of member 22. After a short period of time, (approximately 30 seconds), end 25 has effectively seated against the corner 26 of orifice 24.

I claim:

1. In a cutting instrument having an elongated tubular housing formed with a cutting orifice, a resilient, inner tubular member slidably mounted coaxially within said tubular housing, and driving means for reciprocating said inner tubular member, the improvement comprising:
    means defining a bend in said tubular housing between said driving means and said cutting orifice displacing said cutting orifice in a direction toward said resilient, inner tubular member, such that as the end of said resilient, inner tubular member passes across said cutting orifice, said end is resiliently urged into shearing contact with said cutting orifice.

2. The apparatus of claim 1 in which said cutting orifice is displaced by said bend a distance toward said resilient, inner tubular member which exceeds the clearance between said housing and said inner tubular member.

3. The apparatus of claim 1 in which said cutting orifice is displaced by said bend a distance toward said resilient, inner tubular member which exceeds the clearance between said housing and said inner tubular member by a factor of between two and six.

4. The apparatus of claim 1 in which said housing comprises first and second cylindrical sections joined by an intermediate section, said first section having a smaller inner diameter than said second section, said orifice being located in said first section, and said bend displacing said first section angularly with respect to said second section.

5. The apparatus of claim 1 in which said inner tubular member is made of full-hard stainless steel and said tubular housing is made of fully annealed stainless steel.

6. In an ophthalmic instrument for removing vitreous and the like from the eye having an elongated, tubular housing with an outer diameter less than 0.100 inch formed with a cutting orifice, an inner, resilient tubular member slidably mounted coaxially within said tubular housing with a clearance of less than 0.0015 inch, and driving means for reciprocating said inner tubular member, the improvement comprising:
    means defining a bend in said tubular housing between said driving means and said cutting orifice displacing said cutting orifice in a direction toward said inner, resilient tubular member a distance which exceeds said clearance, so that as the end of said inner, resilient tubular member passes across said cutting orifice, said end is resiliently urged into shearing contact with said cutting orifice.

7. In an ophthalmic instrument for removing vitreous, lens and the like, from the eye, having an elongated tubular housing with an open end and a closed end, an orifice formed in said tubular housing, an inner tubular member slidably mounted coaxially within said tubular housing, said inner tubular member providing a passage for the vitreous material, and the like, drive means for producing relative axial movement between said tubular housing and said inner tubular member, means coupling said inner tubular member to a vacuum source to draw vitreous, and the like, up through said inner tubular member; and means for introducing replacement fluid into the eye to maintain constant pressure within the eye; the improvement comprising:
    a bend in said tubular housing between said driving means and said cutting orifice displacing said orifice toward said inner tubular member, such that as the end of said inner tubular member passes across said orifice, said end is resiliently urged into shearing contact with said orifice.

* * * * *